(12) United States Patent
Himmler et al.

(10) Patent No.: US 11,220,511 B2
(45) Date of Patent: Jan. 11, 2022

(54) PROCESS FOR PREPARING SPIROKETAL-SUBSTITUTED CYCLIC KETOENOLS

(71) Applicant: BAYER CROPSCIENCE AKTIENGESELLSCHAFT, Monheim am Rhein (DE)

(72) Inventors: Thomas Himmler, Odenthal (DE); Julia Johanna Hahn, Duesseldorf (DE); Joachim Crede, Wuppertal (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 343 days.

(21) Appl. No.: 16/322,556

(22) PCT Filed: Jul. 31, 2017

(86) PCT No.: PCT/EP2017/069287
§ 371 (c)(1),
(2) Date: Feb. 1, 2019

(87) PCT Pub. No.: WO2018/024659
PCT Pub. Date: Feb. 8, 2018

(65) Prior Publication Data
US 2019/0202837 A1    Jul. 4, 2019

(30) Foreign Application Priority Data

Aug. 4, 2016  (EP) .................... 16182706

(51) Int. Cl.
| | | |
|---|---|---|
| *C07D 491/113* | (2006.01) |
| *C07D 319/08* | (2006.01) |
| *C07D 407/12* | (2006.01) |
| *C07D 317/72* | (2006.01) |
| *A01N 43/90* | (2006.01) |

(52) U.S. Cl.
CPC ........ *C07D 491/113* (2013.01); *C07D 317/72* (2013.01); *C07D 319/08* (2013.01); *C07D 407/12* (2013.01); *A01N 43/90* (2013.01)

(58) Field of Classification Search
CPC .............. C07D 491/113; C07D 319/08; C07D 407/12; C07D 317/72
See application file for complete search history.

(56) References Cited

U.S. PATENT DOCUMENTS

| | | |
|---|---|---|
| 6,589,976 B1 | 7/2003 | Fischer et al. |
| 7,897,543 B2 | 3/2011 | Bretschneider et al. |
| 8,013,172 B2 | 9/2011 | Fischer et al. |
| 8,541,617 B2 | 9/2013 | Fischer et al. |
| 2011/0190493 A1 | 8/2011 | Bretschneider et al. |
| 2014/0045696 A1 | 2/2014 | Bretschneider et al. |

FOREIGN PATENT DOCUMENTS

| | | |
|---|---|---|
| WO | 99/16748 A1 | 4/1999 |
| WO | 2006/089633 A2 | 8/2006 |
| WO | 2007/096058 A1 | 8/2007 |

OTHER PUBLICATIONS

Zhao et al. J. Agric. Food Chem. 2012, 60, 4779-4787 (Year: 2012).*
International Search Report of International Patent Application No. PCT/EP2017/069287 dated Oct. 12, 2017.

* cited by examiner

*Primary Examiner* — Matthew P Coughlin
(74) *Attorney, Agent, or Firm* — McBee Moore & Vanik IP, LLC

(57) ABSTRACT

The invention relates to a novel process for preparing spiroketal-substituted cyclic ketoenols which can be used as insecticides, acaricides or herbicides. The present invention also relates to novel intermediates for the preparation of spiroketal-substituted cyclic ketoenols.

9 Claims, No Drawings

PROCESS FOR PREPARING SPIROKETAL-SUBSTITUTED CYCLIC KETOENOLS

CROSS-REFERENCE TO RELATED APPLICATIONS

This application is a National Stage entry of International Application No. PCT/EP2017/069287, filed 31 Jul. 2017, which claims priority to European Patent Application No. 16182706.8, filed 4 Aug. 2016.

BACKGROUND

Field

The invention relates to a novel process for preparing spiroketal-substituted cyclic ketoenols which can be used as insecticides, acaricides or herbicides. The present invention also relates to novel intermediates for the preparation of spiroketal-substituted cyclic ketoenols.

Description of Related Art

It is already known that certain spiroketal-substituted cyclic ketoenols have insecticidal, acaricidal or herbicidal activity (WO 99/16748; WO 06/089633). One known synthesis (A) of such spiroketal-substituted cyclic ketoenols starts with appropriately spiroketal-substituted cyclohexanones of the general formula (I) which can be converted in a Bucherer-Bergs reaction into the spiroketal-substituted hydantoins of the general formula (II). Alkaline hydrolysis of these hydantoins affords the spiroketal-substituted amino acids of the general formula (III). These amino acids are then esterified by known methods of organic chemistry (for example by reaction with an alcohol $R^7$—OH and thionyl chloride) to give the spiroketal-substituted amino acid esters of the general formula (IV; $R^7$ equals $C_1$-$C_6$-alkyl). These amino acid esters are then acylated at the nitrogen with phenylacetyl chlorides of the general formula (VII) to give the compounds of the general formula (VIII). The compounds of the general formula (VIII) are subsequently cyclized in a Dieckmann reaction by action of a strong base such as potassium tert-butoxide or sodium methoxide, affording the spiroketal-substituted cyclic ketoenols of the general formula (XI). This process (A) is shown in Scheme 1. A considerable disadvantage of this process (A) is the fact that, during the esterification of the amino acids of the general formula (III) under acidic conditions, there is almost always at least partial reketalisation of the cyclic ketal to an acyclic ketal (geminal bis(alkoxy) compound) of the general formula (V). Moreover, it was found in practice that even under conditions which are anhydrous in principle, additional ketones of the general formula (VI) may be formed, even if only in lower amounts. The ester is then consequently obtained as a mixture of at least two products of the general formulae (IV) and (V), resulting in corresponding product mixtures in the subsequent stages of process (A), too. In addition, the fact that the acyclic ketals are easily hydrolyzed also leads to the formation of N-acylated ketones of the general formula (X) (identical to the products of the N-acylation of the keto compounds of the general formula (VI)). Thus, after N-acylation with a phenylacetyl chloride of the general formula (VII), the amides of the general formulae (VIII), (IX) and (X) are obtained. Dieckmann cyclization then leads to a mixture of the cyclic ketoenols of the general formulae (XI), (XII) and (XIII). Accordingly, in order to obtain a clean product of the general formula (XI) under industrial conditions (where, for example, purification of the target compound by chromatography is not an option), it is essential to convert, in an additional step, this mixture of the compounds of the general formulae (XI), (XII) and (XIII) with a diol of the general formula (XIV) in the presence of an acidic catalyst into the uniform compound of the general formula (XI). This additional step is time-consuming, cost-intensive and uneconomical.

Scheme 1: Process A

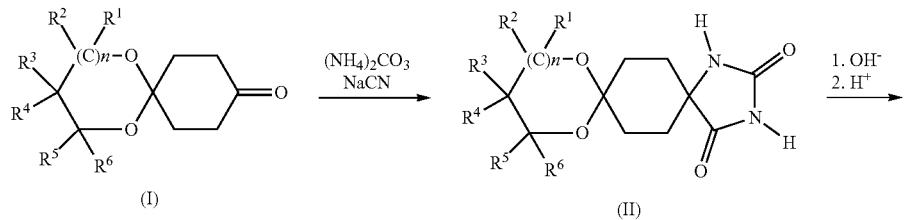

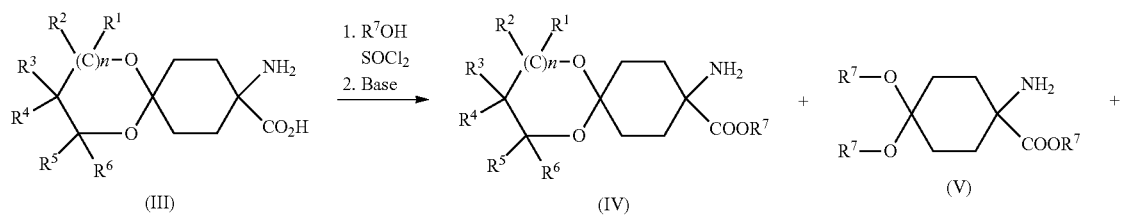

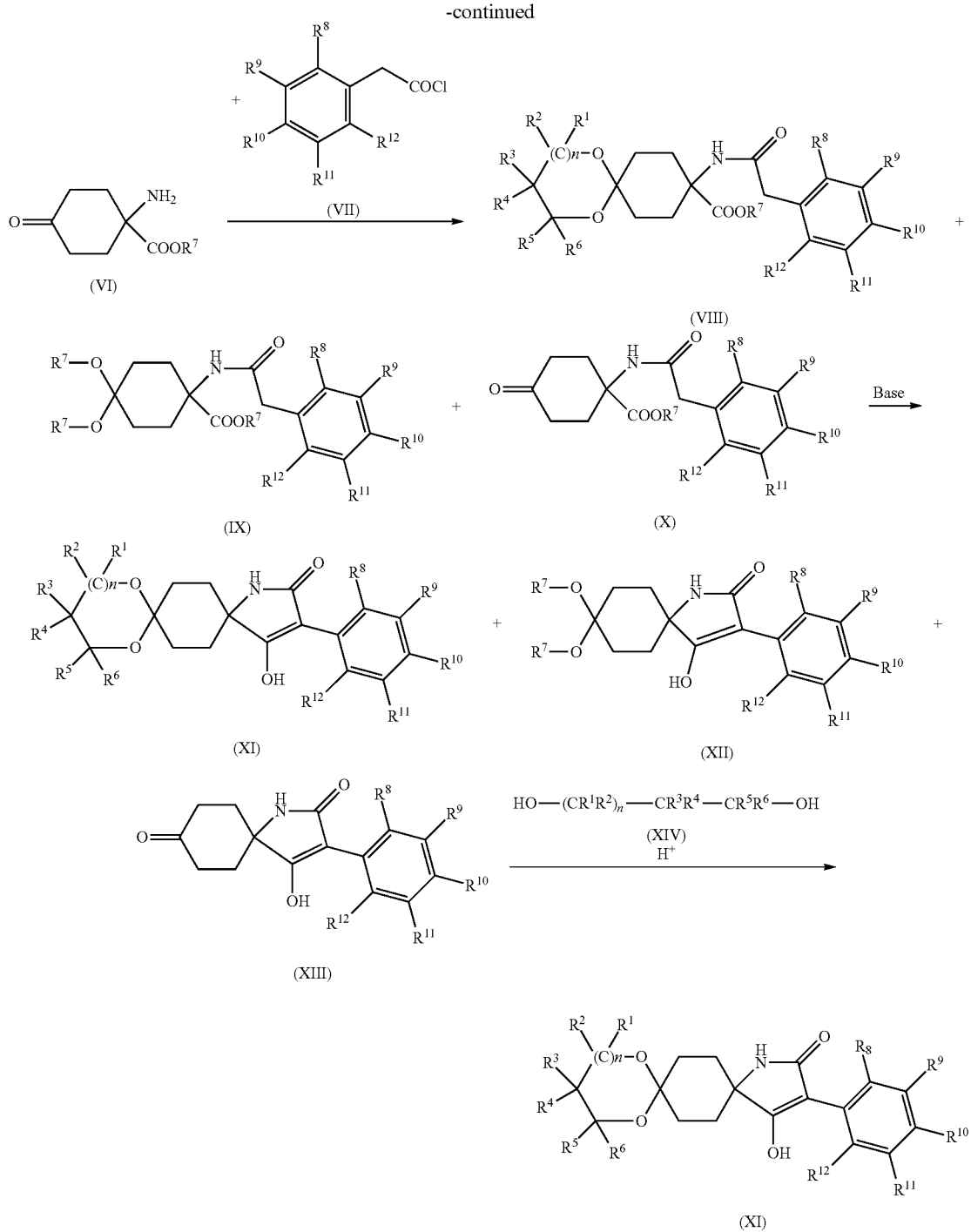

There was therefore a need for a more simple, shorter process for the preparation of spiroketal-substituted cyclic ketoenols of the general formula (XI).

SUMMARY

It has now been found that the synthesis of spiroketal-substituted cyclic ketoenols of the general formula (XI) can, surprisingly, be simplified by acylating the spiroketal-substituted amino acids of the general formula (III) in a first step (1) at the nitrogen under Schotten-Baumann conditions with a phenylacetyl chloride of the general formula (VII), giving the amides of the general formula (XV); then, in the second step (2) of the process according to the invention, carrying out an esterification under acidic conditions with the diol of the general formula (XIV), which may yield a mixture of the esters of the general formula (XVI) and diesters of the general formula (XVII); and then, in the third step (3) of the process according to the invention, carrying out the Dieckmann cyclization to afford the spiroketal-substituted cyclic ketoenols of the general formula (XI). The process (B) according to the invention is shown in Scheme 2.

Scheme 2: Process B
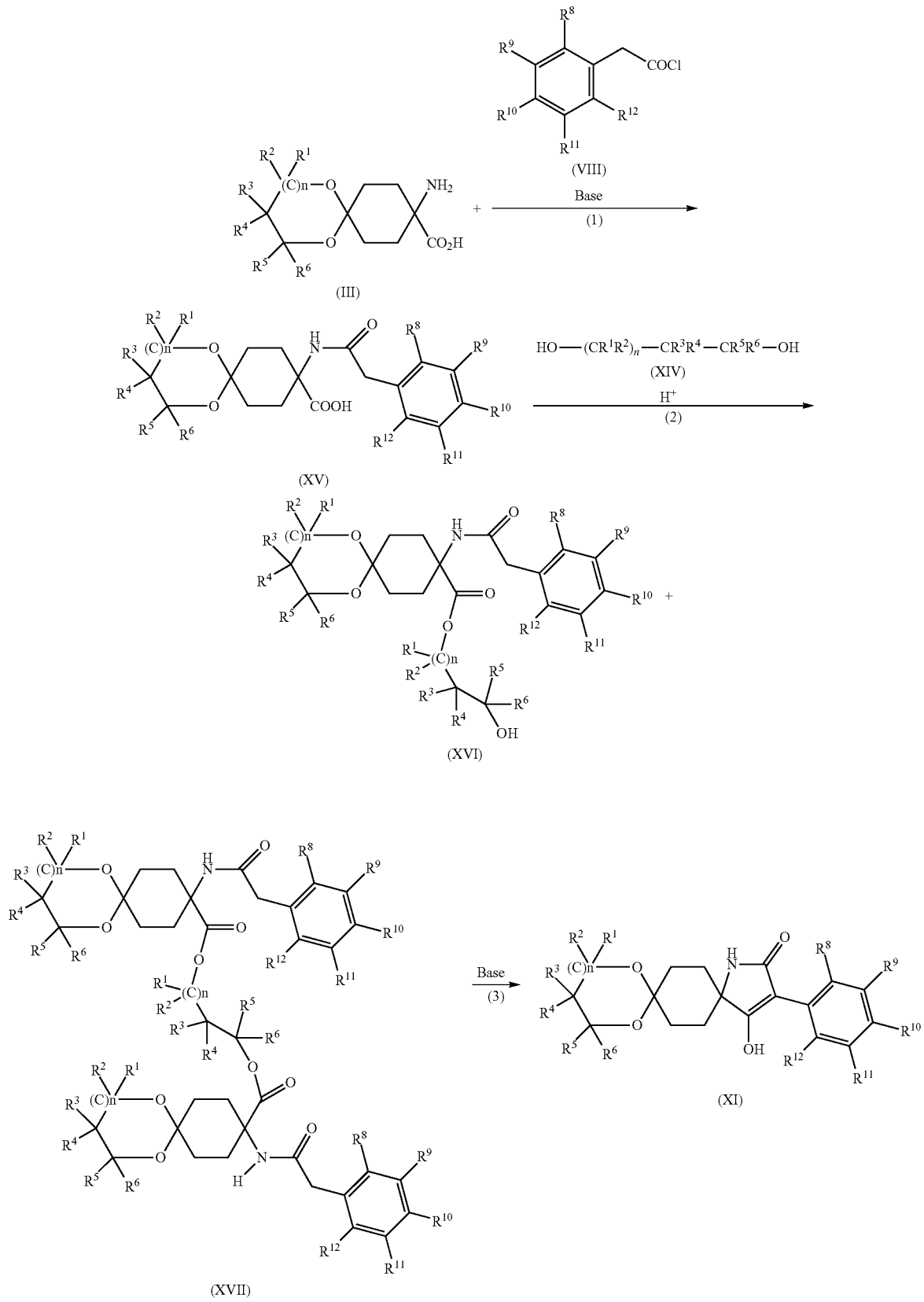

DETAILED DESCRIPTION OF A PREFERRED EMBODIMENT

The present invention therefore comprises a novel process (B) for the preparation of spiroketal-substituted cyclic ketoenols of the general formula (XI), characterized in that, in the first step (1) of the process, spiroketal-substituted amino acids of the general formula (III)

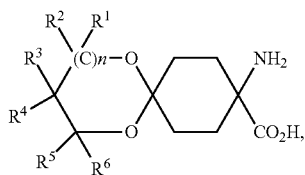

(III)

where the radicals
$R^1$ to $R^6$ independently of one another represent hydrogen, methyl, ethyl or phenyl
and
n represents 0 or 1,
are reacted in the presence of a base with a phenylacetyl chloride of the general formula (VII)

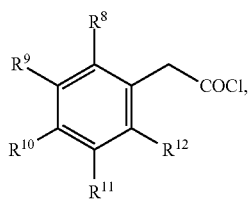

(VII)

where the radicals
$R^8$ to $R^{12}$ independently of one another represent hydrogen, methyl, ethyl, fluoroalkyl having one or 2 carbon atoms and one to five fluorine atoms, halogen, methoxy, ethoxy, trifluoromethoxy or optionally methyl-, ethyl-, methoxy-, ethoxy- or halogen-substituted phenyl,
to give compounds of the general formula (XV)

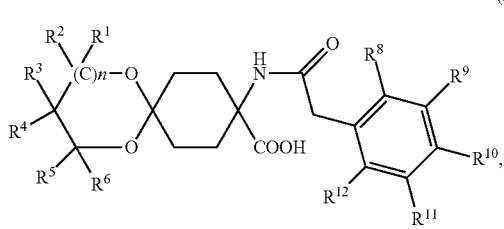

(XV)

where n and the radicals
$R^1$ to $R^6$ and $R^8$ to $R^{12}$ have the meanings given above;
then, in the second step (2) of the process according to the invention (B), a compound of general formula (XV) is esterified with an α,ω-diol of the general formula (XIV)

$$HO—(CR^1R^2)_n—CR^3R^4—CR^5R^6—OH \quad (XIV),$$

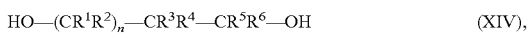

where n and the radicals $R^1$ to $R^6$ have the meanings given above and are, in the concrete individual case, identical to those in the compound of the general formula (XV), in the presence of an acid as catalyst, to give the mono- and diesters of the general formulae (XVI) and (XVII)

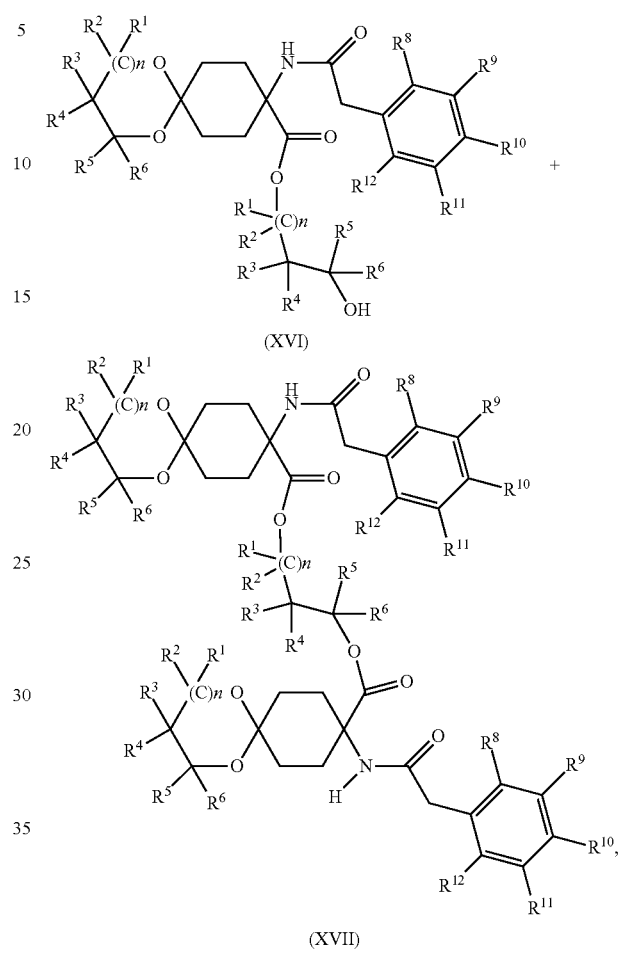

where n and the radicals $R^1$ to $R^6$ and $R^8$ to $R^{12}$ have the meanings given above and both n and the corresponding radicals $R^1$ to $R^6$ and $R^8$ to $R^{12}$ at the two positions of the compounds of the general formulae (XVI) or (XVII) are identical;
subsequently, in the third step (3) of the process according to the invention (B), the compounds of general formulae (XVI) and (XVII), where n and the radicals $R^1$ to $R^6$ and $R^8$ to $R^{12}$ have the meanings given above,
are converted by reaction with a strong base into the spiroketal-substituted cyclic ketoenols of the general formula (XI)

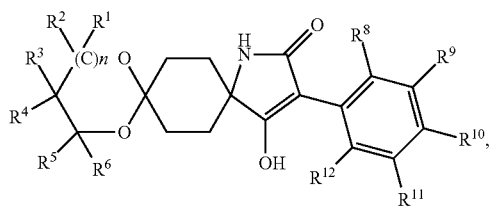

(XI)

where n and the radicals $R^1$ to $R^6$ and $R^8$ to $R^{12}$ have the meanings given above.

$R^1$ to $R^6$ represents $R^1$, $R^2$, $R^3$, $R^4$, $R^5$, $R^6$.

$R^8$ to $R^{12}$ represents $R^8$, $R^9$, $R^{10}$, $R^{11}$, $R^{12}$.

In the formulae (III), (VII), (XV), (XIV), (XVI), (XVII), (XI), $R^1$ to $R^6$ independently of one another preferably represent hydrogen, methyl or ethyl, $R^8$ to $R^{12}$ independently of one another preferably represent hydrogen, methyl, ethyl, fluorine, chlorine, methoxy, ethoxy, trifluoromethoxy or optionally methyl-, ethyl-, methoxy-, ethoxy-, fluorine-, chlorine- or bromine-substituted phenyl, n preferably represents 0 or 1;

$R^1$ to $R^6$ independently of one another particularly preferably represent hydrogen or methyl, $R^8$ to $R^{12}$ independently of one another particularly preferably represent hydrogen, methyl, ethyl, fluorine, chlorine, methoxy, ethoxy or optionally methyl-, ethyl-, methoxy-, ethoxy-, fluorine- or chlorine-substituted phenyl, n particularly preferably represents 0 or 1;

$R^3$ to $R^6$ independently of one another also particularly preferably represent hydrogen or methyl, $R^8$ to $R^{12}$ independently of one another also particularly preferably represent hydrogen, methyl, ethyl, fluorine, chlorine, methoxy, ethoxy or optionally methyl-, methoxy-, fluorine- or chlorine-substituted phenyl, n also particularly preferably represents 0;

$R^3$ to $R^6$ independently of one another very particularly preferably represent hydrogen or methyl, $R^8$ to $R^{12}$ independently of one another very particularly preferably represent hydrogen, methyl or chlorine, n very particularly preferably represents 0.

With emphasis, n represents 0, $R^3$ to $R^6$ represent hydrogen, $R^8$ represents methyl, $R^9$ represents hydrogen, $R^{10}$ represents chlorine, $R^{11}$ represents hydrogen, $R^{12}$ represents methyl.

With emphasis, n represents 0, $R^3$ to $R^6$ represent hydrogen, $R^8$ represents methyl, $R^9$ represents hydrogen, $R^{10}$ represents methyl, $R^{11}$ represents hydrogen, $R^{12}$ represents methyl.

With emphasis, n represents 0, $R^3$ represents hydrogen, $R^4$ represents methyl, $R^5$ represents hydrogen, $R^6$ represents methyl, $R^8$ represents methyl, $R^9$ represents hydrogen, $R^{10}$ represents hydrogen, $R^{11}$ represents methyl, $R^{12}$ represents hydrogen.

With emphasis, n represents 1, $R^1$ represents hydrogen, $R^2$ represents hydrogen, $R^3$ represents methyl, $R^4$ represents methyl, $R^5$ represents hydrogen, $R^6$ represents hydrogen, $R^8$ represents methyl, $R^9$ represents hydrogen, $R^{10}$ represents chlorine, $R^{11}$ represents hydrogen, $R^{12}$ represents methyl.

With emphasis, n represents 1, $R^1$ to $R^6$ represent hydrogen, $R^8$ represents methyl, $R^9$ represents hydrogen, $R^{10}$ represents chlorine, $R^{11}$ represents hydrogen, $R^{12}$ represents methyl.

In the formulae (I), (II) and (XIII), described in Process A, $R^1$, $R^2$, $R^3$, $R^4$, $R^5$, $R^6$, $R^8$, $R^9$, $R^{10}$, $R^{11}$, $R^{12}$ and n have the meanings mentioned above.

In the formulae (IV), (VIII), (IX), (X) and (XII), described in Process A, $R^1$, $R^2$, $R^3$, $R^4$, $R^5$, $R^6$, $R^7$, $R^8$, $R^9$, $R^{10}$, $R^{11}$, $R^{12}$ and n have the meanings mentioned above and $R^7$ represents $C_1$-$C_6$-alkyl. With particular emphasis, n represents 0; $R^3$ to $R^6$ represent hydrogen; $R^8$ and $R^{12}$ represent methyl; $R^9$ and $R^{11}$ represent hydrogen; $R^{10}$ represents chlorine and $R^7$ represents methyl:

Compound of the formula (IV-1):

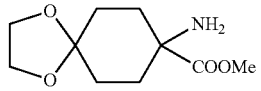

Compound of the formula (VIII-1):

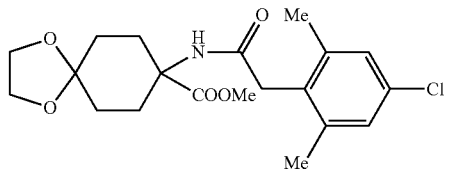

Compound of the formula (IX-1):

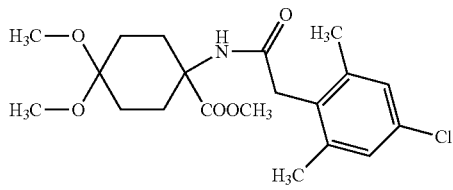

Compound of the formula (X-1):

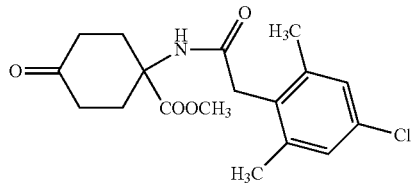

Compound of the formula (XII-1):

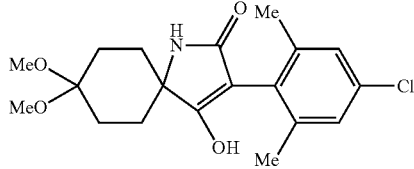

In the formulae (V) and (VI), described in Process A, $R^7$ represents $C_1$-$C_6$-alkyl. With particular emphasis, $R^7$ represents methyl:

Compound of the formula (V-1):

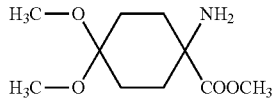

Compound of the formula (VI-1):

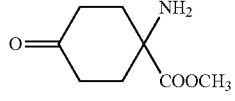

(Me=CH$_3$=methyl)

The first step (1) of the process according to the invention (B) is carried out in a solvent which is inert under the reaction conditions. Possible solvents include, for example: dichloromethane, toluene, ortho-, meta- or para-xylene, mesitylene, chlorobenzene, ortho-dichlorobenzene, acetonitrile, butyronitrile, N,N-dimethylformamide, N,N-dimethylacetamide, tetrahydrofuran, 2-methyltetrahydrofuran, cyclopentylmethylether, methyl tert-butyl ether, tert-amyl methyl ether, 1,4-dioxane, ethyl acetate, butyl acetate, water or mixtures of these solvents. Preference is given to toluene, ortho-, meta- or para-xylene, chlorobenzene, acetonitrile, butyronitrile, tetrahydrofuran, 2-methyltetrahydrofuran, cyclopentylmethylether, methyl tert-butyl ether, tert-amyl methyl ether, ethyl acetate, butyl acetate, water or mixtures of these solvents. Particular preference is given to mixtures of toluene, ortho-, meta- or para-xylene, chlorobenzene, 2-methyltetrahydrofuran, cyclopentyl methyl ether, methyl tert-butyl ether, tert-amyl methyl ether with water (Schotten-Baumann conditions).

Suitable bases for use in the first step (1) of the process according to the invention (B) are organic bases such as, for example, trimethylamine, triethylamine, piperidine, morpholine, pyridine; or inorganic bases such as ammonia, lithium hydroxide, sodium hydroxide, potassium hydroxide, sodium carbonate, potassium carbonate, sodium bicarbonate, potassium bicarbonate, calcium carbonate. Preference is given to sodium hydroxide and potassium hydroxide.

Solid inorganic bases can be employed as solids or in the form of their aqueous solutions. Preference is given to using aqueous solutions.

The base is usually employed in such an amount that the resulting pH is between 10 and 14. Preferably, the reactions are carried out at a pH between 11 and 13.

The first step (1) of the process according to the invention (B) is carried out at temperatures between −5 and 50° C.; preferably between 0 and 30° C.

Isolation of the compounds of the general formula (XV) is carried out by customary methods of organic chemistry such as filtration, phase separation or extraction.

In the second step (2) of the process according to the invention (B), use may be made of solvents which are inert under the reaction conditions. Possible solvents include, for example: dichloromethane, toluene, ortho-, meta- or para-xylene, mesitylene, chlorobenzene, ortho-dichlorobenzene, acetonitrile, butyronitrile, tetrahydrofuran, 2-methyltetrahydrofuran, cyclopentylmethylether, methyl tert-butyl ether, tert-amyl methyl ether, 1,4-dioxane or mixtures of these solvents. Preference is given to toluene, ortho-, meta- or para-xylene, chlorobenzene, acetonitrile, butyronitrile, 2-methyltetrahydrofuran, cyclopentylmethylether, methyl tert-butyl ether, tert-amyl methyl ether or mixtures of these solvents.

The α,ω-diol of the general formula (XIV) is employed in an amount of at least 0.5 mol per 1 mol of the compound of the general formula (XV). It is also possible to work in any excess of α,ω-diol of the general formula (XIV), thus simultaneously using the latter as solvent.

The second step (2) of the process according to the invention (B) is carried out in the presence of a catalytic amount of an acid. Possible acids include, for example: hydrogen chloride, sulfuric acid, methanesulfonic acid, trifluoromethanesulfonic acid, para-toluenesulfonic acid or acidic ion exchange resins such as, for example, Amberlite. Preference is given to using sulfuric acid or para-toluenesulfonic acid. Particular preference is given to using sulfuric acid.

The acid is employed in amounts from 0.01 to 20 percent by weight, based on the compound of the general formula (XV). Preference is given to 0.05 to 10 percent by weight.

The second step (2) of the process according to the invention (B) is carried out at temperatures between 20 and 150° C.; preferably between 50 and 120° C.

Isolation of the compounds of the general formulae (XVI) and (XVII) is carried out by customary methods of organic chemistry such as filtration, phase separation or extraction.

In the third step (3) of the process according to the invention (B), use may be made of solvents which are inert under the reaction conditions. Possible solvents include, for example: toluene, ortho-, meta- or para-xylene, mesitylene, chlorobenzene, ortho-dichlorobenzene, acetonitrile, butyronitrile, tetrahydrofuran, 2-methyltetrahydrofuran, cyclopentylmethylether, methyl tert-butyl ether, tert-amyl methyl ether, 1,4-dioxane, N,N-dimethylformamide, N,N-dimethylacetamide, N-methylpyrrolidone, methanol, ethanol, 1-butanol, tert-butanol or mixtures of these solvents. Preference is given to N,N-dimethylformamide, N,N-dimethylacetamide, N-methylpyrrolidone, methanol, tert-butanol or mixtures of these solvents.

Suitable for use as bases in the third step (3) of the process according to the invention (B) are, for example, sodium hydroxide, potassium hydroxide, sodium methoxide, potassium methoxide, sodium ethoxide, potassium ethoxide, sodium tert-butoxide or potassium tert-butoxide. Preference is given to sodium hydroxide, sodium methoxide and potassium tert-butoxide. Particular preference is given to using sodium methoxide.

The bases are employed in an amount of from 0.9 to 4 molar equivalents, based on the compounds of the general formulae (XVI) and (XVII). Preference is given to using 1 to 3.5 molar equivalents.

The temperature in the third step (3) of the process according to the invention (B) is between 20 and 150° C. Preferably, the reactions are carried out between 40 and 100° C.

Isolation of the compounds of the general formula (XI) after adjustment of the pH of the reaction mixture to a value between 0 and 8 is carried out by customary methods of organic chemistry such as filtration, phase separation or extraction.

Some of the compounds of the formula (III) are known (WO 06/089633), some are novel, or can be prepared by the methods described therein.

Some of the compounds of the formula (VII) are known (WO 97/02243), some are novel, or can be prepared by the methods described therein.

The compounds of the formula (XIV) are commercially available.

The present invention also provides the novel compound 1-{[(4-chloro-2,6-dimethylphenyl)acetyl]amino}-4-oxocyclohexanecarboxylic acid (XV-1)

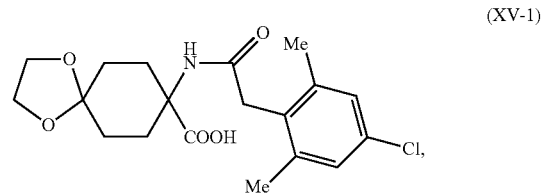 [SMILES: Cc1cc(Cl)cc(C)c1CC(=O)NC1(C(=O)O)CCC2(CC1)OCCO2]

(XV-1)

Some of the amino acids of the general formula (III) required for preparing the compounds of the general formula (XV) are novel. The yields achieved in their preparation by alkaline hydrolysis of the corresponding hydantoins of the general formula (II), followed by adjustment to a pH below 7 and removal of the inorganic salts, are not always satisfactory. Thus, for example, WO 06/089633 describes the preparation of the compound 8-amino-1,4-dioxaspiro[4.5]

decane-8-carboxylic acid (III-1) by boiling the compound 9,12-dioxa-1,3-diazadispiro[4.2.4.2]tetradecane-2,4-dione (II-1) with 9.8 molar equivalents of potassium hydroxide in the form of 30% strength aqueous potassium hydroxide solution. Using conc. hydrochloric acid, the pH is subsequently adjusted to 5.2-5.3. After filtration, the filtrate is concentrated by azeotropic distillation with methanol to about half of the original volume. The potassium chloride is filtered off with suction and the filtrate is further azeotropically dewatered with methanol. The isolated yield of target compound is only 46% of theory. In a further published process (*Journal of Agricultural and Food Chemistry* 2012 (60) 4779-4787), the hydantoin (II-1) is boiled under reflux with 7 molar equivalents of sodium hydroxide in the form of 3 N aqueous sodium hydroxide solution for 4 days. The mixture is then cooled to 0° C. and the pH is adjusted to 6 with conc. hydrochloric acid. After filtration, the filtrate is concentrated under reduced pressure to about one third of the original volume. The precipitated solid was filtered off with suction and dried. The yield of target compound was only 48% of theory.

There was therefore a demand for an improved process for preparing a precursor suitable for the preparation of the compounds of the general formula (XV#)

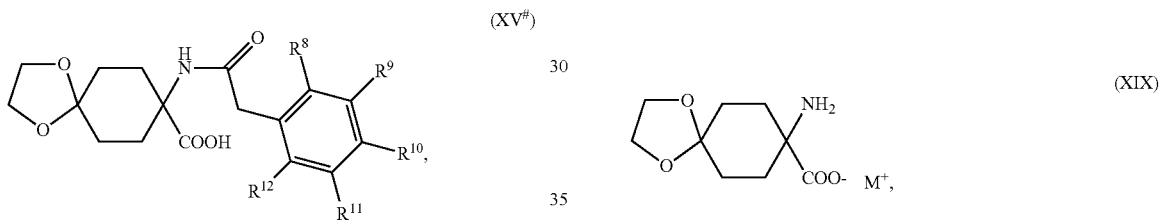

where the radicals $R^8$ to $R^{12}$ have the meanings given above.

It has now surprisingly been found that, instead of the amino acid (III-1), its corresponding sodium or potassium salts of the general formula (XIX)

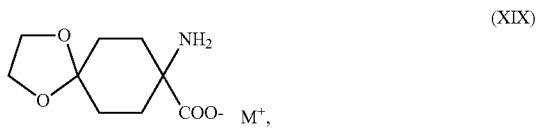

in which
M represents sodium or potassium
can be obtained in a simple manner and in high yield.

Accordingly, the present invention also provides a novel process (C) for the preparation of compounds of the general formula (XIX), characterized in that the hydantoin of the formula (II-1, 9,12-dioxa-1,3-diazadispiro[4.2.4.2]tetradecane-2,4-dione) is heated under reflux with aqueous sodium hydroxide solution or aqueous potassium hydroxide solution and the resulting compound of the general formula (XIX) is then isolated by filtration.

The sodium hydroxide or potassium hydroxide is employed in amounts of from 1 to 10 molar equivalents. Preference is given to using from 2 to 7 equivalents. If the sodium hydroxide or potassium hydroxide is employed in these amounts, the compound of the formula (XIX) precipitates as a solid.

Particular preference is given to using sodium hydroxide.

The amount of water is from 250 to 1500 ml per mole of hydantoin. Preferably, from 300 to 1000 ml are used per mole of hydantoin.

The reaction temperature is between 50° C. and 200° C. Preferably work is carried out between 80° C. and 150° C.

The reaction can also be carried out at reduced or elevated pressure.

The compounds of the general formula (XIX) are isolated by simple filtration. After analytical content determination, they can be used without further purification instead of the free amino acids in the Schotten-Baumann reaction for preparing the compound (XV#), which at the same time also saves one equivalent of base, which constitutes a further advantage of this process.

The present invention also provides the novel compounds of the general formula (XIX)

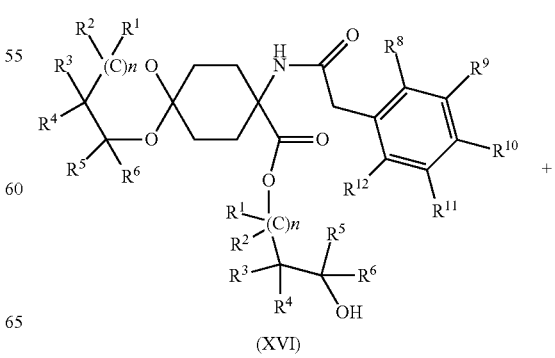

in which

M represents sodium or potassium.

Preference is given to the compound of the general formula (XIX) in which

M represents sodium.

The present invention also provides a novel process (D) for preparing compounds of the general formulae (XVI) and (XVII)

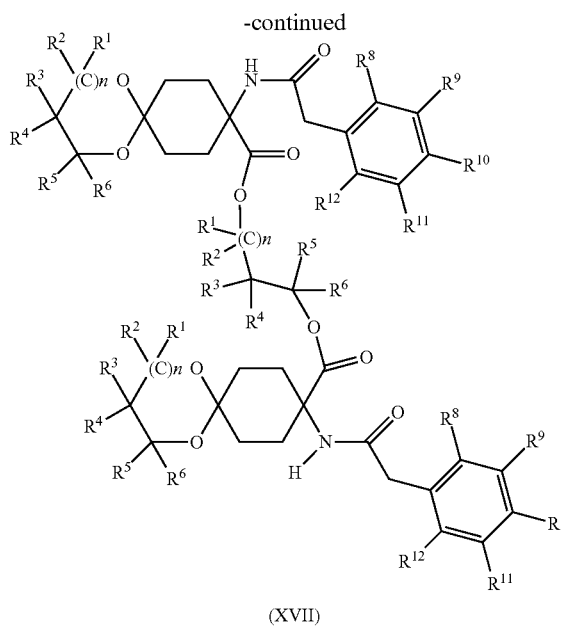

(XVII)

where the radicals
$R^1$ to $R^6$ and $R^8$ to $R^{12}$ have the meanings given above and the corresponding radicals $R^1$ to $R^6$ and $R^8$ to $R^{12}$ at the two positions of the compounds of the general formulae (XVI) or (XVII) are identical and
n represents 0 or 1
and is identical at the two positions of the compounds of the general formulae (XVI) or (XVII),
characterized in that a keto compound of the general formula (XVIII)

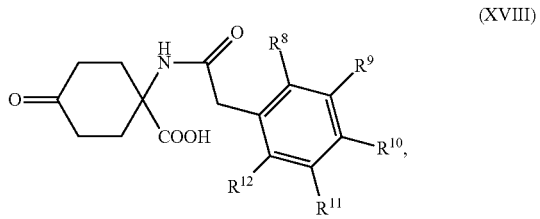

(XVIII)

where the radicals $R^8$ to $R^{12}$ have the meanings given above, is reacted with an α,ω-diol of the general formula (XIV)

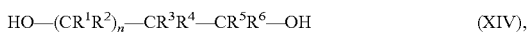

HO—(CR$^1$R$^2$)$_n$—CR$^3$R$^4$—CR$^5$R$^6$—OH    (XIV), where n and the radicals $R^1$ to $R^6$ have the meanings given above and are, in the concrete individual case, identical to those in the compound of the general formula (XVI) or (XVII),
in the presence of an acid as catalyst.

The compounds of the general formula (XVIII) used as starting materials in the process according to the invention (D) are known in principle (WO 06/089633).

In the process according to the invention (D), solvents which are inert under the reaction conditions may be employed. Possible solvents include, for example: dichloromethane, toluene, ortho-, meta- or para-xylene, mesitylene, chlorobenzene, ortho-dichlorobenzene, acetonitrile, butyronitrile, tetrahydrofuran, 2-methyltetrahydrofuran, cyclopentylmethylether, methyl tert-butyl ether, tert-amyl methyl ether, 1,4-dioxane or mixtures of these solvents.

Preference is given to toluene, ortho-, meta- or para-xylene, chlorobenzene, acetonitrile, butyronitrile, 2-methyltetrahydrofuran, cyclopentylmethylether, methyl tert-butyl ether, tert-amyl methyl ether or mixtures of these solvents.

The α,ω-diol of the general formula (XIV) is employed in an amount of at least 2 mol per 1 mol of the compound of the general formula (XVIII). It is also possible to work in any excess of α,ω-diol of the general formula (XIV), simultaneously using the latter as solvent.

Process (D) according to the invention is carried out in the presence of a catalytic amount of an acid. Possible acids include, for example: hydrogen chloride, sulfuric acid, methanesulfonic acid, trifluoromethanesulfonic acid, para-toluenesulfonic acid or acidic ion exchange resins such as, for example, Amberlite. Preference is given to using sulfuric acid or para-toluenesulfonic acid.

The acid is employed in amounts from 0.01 to 20 percent by weight, based on the compound of the general formula (XVIII). Preference is given to 0.05 to 10 percent by weight.

The process according to the invention (D) is carried out at temperatures between 20 and 150° C.; preferably between 50 and 120° C.

Isolation of the compounds of the general formulae (XVI) and (XVII) is carried out by customary methods of organic chemistry such as filtration, phase separation or extraction.

The present invention also provides novel compounds of the general formulae (XVI) and (XVII)

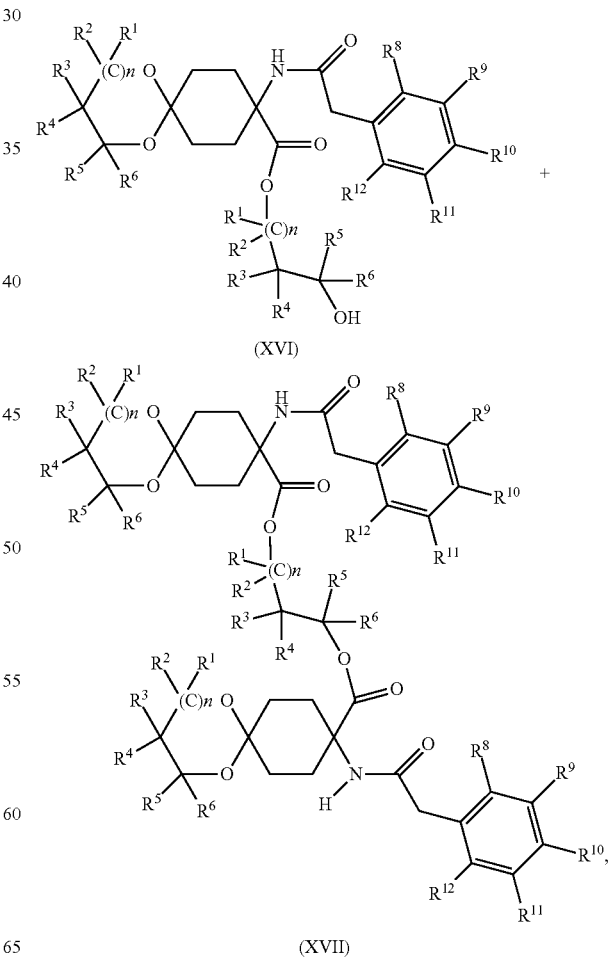

(XVI)

(XVII)

where the radicals
R¹ to R⁶ independently of one another represent hydrogen, methyl, ethyl or phenyl and are identical at the two positions of the compounds of the general formulae (XVI) or (XVII),
n represents 0 or 1,
and is identical at the two positions of the compounds of the general formulae (XVI) or (XVII),
and the radicals
R⁸ to R¹² independently of one another represent hydrogen, methyl, ethyl, fluoroalkyl having one or 2 carbon atoms and one to five fluorine atoms, halogen, methoxy, ethoxy, trifluoromethoxy or optionally methyl-, ethyl-, methoxy-, ethoxy- or halogen-substituted phenyl,
and are identical at the two positions of the compounds of the general formulae (XVI) or (XVII).

Preference is given to novel compounds of the general formulae (XVI) and (XVII) in which the radicals
R¹ to R⁶ independently of one another represent hydrogen, methyl or ethyl
and are identical at the two positions of the compounds of the general formulae (XVI) or (XVII),
n represents 0 or 1
and is identical at the two positions of the compounds of the general formulae (XVI) or (XVII)
and the radicals
R⁸ to R¹² independently of one another represent hydrogen, methyl, ethyl, fluorine, chlorine, methoxy, ethoxy, trifluoromethoxy or optionally methyl-, ethyl-, methoxy-, ethoxy-, fluorine-, chlorine- or bromine-substituted phenyl
and are identical at the two positions of the compounds of the general formulae (XVI) or (XVII).

Particular preference is given to novel compounds of the general formulae (XVI) and (XVII) in which the radicals
R¹ to R⁶ independently of one another represent hydrogen or methyl
and are identical at the two positions of the compounds of the general formulae (XVI) or (XVII),
n represents 0
and the radicals
R⁸ to R¹² independently of one another represent hydrogen, methyl, ethyl, fluorine, chlorine, methoxy, ethoxy or optionally methyl-, ethyl-, methoxy-, ethoxy-, fluorine- or chlorine-substituted phenyl
and are identical at the two positions of the compounds of the general formulae (XVI) or (XVII).

Very particular preference is given to
2-hydroxyethyl 8-{[(4-chloro-2,6-dimethylphenyl)acetyl]amino}-1,4-dioxaspiro[4.5]decane-8-carboxylate ((XVI) where n=0, R³ to R⁶ represents hydrogen, R⁸ and R¹² represent methyl, R⁹ and R¹¹ represent hydrogen, R¹⁰ represents chlorine),
ethane-1,2-diyl bis(8-{[(2,5-dimethylphenyl)acetyl]amino}-1,4-dioxaspiro[4.5]decane-8-carboxylate) ((XVII) where n=0, R³ to R⁶ represent hydrogen, R⁸ and R¹² represent methyl, R⁹ and R¹¹ represent hydrogen, R¹⁰ represents chlorine),
3-hydroxybutan-2-yl 8-{[(2,5-dimethylphenyl)acetyl]amino}-2,3-dimethyl-1,4-dioxaspiro[4.5]decane-8-carboxylate ((XVI) where n=0, R³ and R⁵ represent hydrogen, R⁴ and R⁶ represent methyl, R⁸ and R¹¹ represent methyl, R⁹, R¹¹ and R¹² represent hydrogen),
3-hydroxy-2,2-dimethylpropyl 9-{[(4-chloro-2,6-dimethylphenyl)acetyl]amino}-3,3-dimethyl-1,5-dioxaspiro[5.5]undecane-9-carboxylate (((XVI) where n=1, R¹, R², R⁵ and R⁶ represent hydrogen, R³ and R⁴ represent methyl, R⁹ and R¹¹ represent hydrogen, R⁸ and R¹² represent methyl, R¹⁰ represents chlorine).

The present invention will be described in more detail by the examples below, without being limited thereby.

Example 1

2-Hydroxyethyl 8-{[(4-chloro-2,6-dimethylphenyl)acetyl]amino}-1,4-dioxaspiro[4.5]decane-8-carboxylate (Ex. XVI-1) and ethane-1,2-diyl bis(8-{[(2,5-dimethylphenyl)acetyl]amino}-1,4-dioxaspiro[4.5]decane-8-carboxylate) (Ex. (XVII-1)

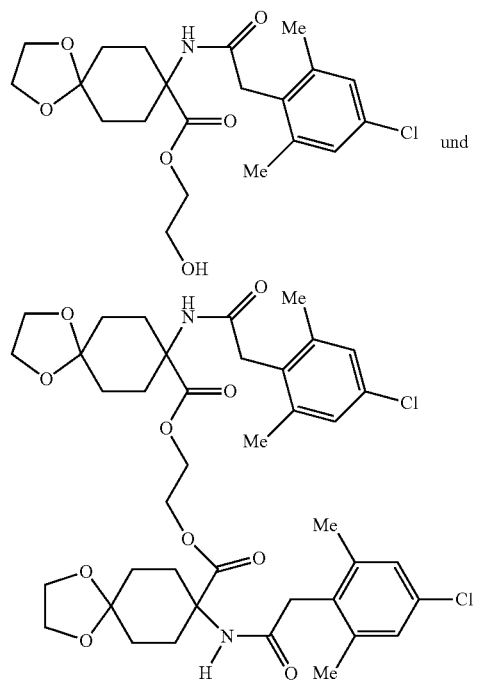

und 1.862 g [30 mmol] of ethylene glycol and 10 drops of conc. sulfuric acid are added to a solution of 3.82 g [10 mmol] of 8-{[(4-chloro-2,6-dimethylphenyl)acetyl]amino}-1,4-dioxaspiro[4.5]decane-8-carboxylic acid in 15 ml of chlorobenzene. The reaction mixture is heated at 88 to 103° C. for 9 hours. After 5 hours, a further 8 drops of conc. sulfuric acid are added. The reaction mixture is cooled to room temperature, diluted with 30 ml of chlorobenzene and filtered. The filter residue is washed with petroleum ether, dissolved in methylene chloride and washed with saturated aqueous sodium bicarbonate solution and water. Drying of the organic phase over sodium sulfate and concentration under reduced pressure gives 3.00 g of a colourless solid which, according to HPLC, contains 68.8% of 2-hydroxyethyl 8-{[(4-chloro-2,6-dimethylphenyl)acetyl]amino}-1,4-dioxaspiro[4.5]decane-8-carboxylate (48.5% of theory) and 14.1% of ethane-1,2-diyl bis(8-{[(2,5-dimethylphenyl)acetyl]amino}-1,4-dioxaspiro[4.5]decane-8-carboxylate) (10.7% of theory).

LC/MS (ESI positive): m/e=426 (MH⁺, 1 ³⁵Cl).

LC/MS (ESI positive): m/e=788 (MH⁺, 2 ³⁵Cl).

¹H-NMR (600 MHz, CDCl₃): δ=1.25-1.35 (m; 2H), 1.6-1.7 (m; 2H), 1.8-1.9 (m; 2H), 2.05-2.15 (m; 2H), 2.24 (s; 6H), 2.9 (s, br; 1H), 3.51 (s; 2H), 3.7 (m, br; 2H), 3.85 (s; 4H), 4.24 (m; 2H), 5.48 (s; 1H), 7.04 (s; 2H) ppm.

¹H-NMR (600 MHz, CDCl₃): δ=1.25-1.35 (m; 4H), 1.6-1.7 (m; 4H), 1.8-1.9 (m; 4H), 2.05-2.15 (m; 4H), 2.23-2.25 (s; 12H), 3.48 (s; 4H), 3.85 (s; 4H), 4.24 (m; 4H), 5.48 (s; 1H), 7.03 (s; 4H) ppm.

Example 2

2-Hydroxyethyl 8-{[(4-chloro-2,6-dimethylphenyl)acetyl]amino}-1,4-dioxaspiro[4.5]decane-8-carboxylate (Ex. XVI-1)

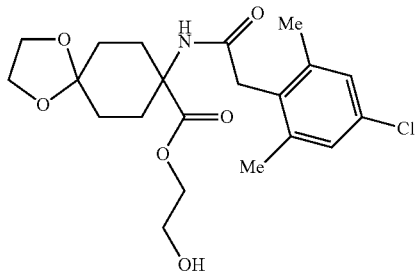 [SMILES: Cc1cc(Cl)cc(C)c1CC(=O)NC1(C(=O)OCCO)CCC2(CC1)OCCO2]

2.483 g [40 mmol] of ethylene glycol and 5 drops of conc. sulfuric acid are added to a solution of 1.689 g [5 mmol] of 1-{[(4-chloro-2,6-dimethylphenyl)acetyl]amino}-4-oxocyclohexanecarboxylic acid in 7.5 ml of chlorobenzene. The reaction mixture is heated at 100 to 105° C. for 4.5 hours and then, at room temperature, stirred with water and methylene chloride. The organic phase is separated off, washed with water, dried over sodium sulfate and concentrated under reduced pressure. This gives 1.98 g of a colourless solid which, according to HPLC, contains 83.1% of the title compound (77.3% of theory).

Example 3

3-Hydroxy-2,2-dimethylpropyl 9-{[(4-chloro-2,6-dimethylphenyl)acetyl]amino}-3,3-dimethyl-1,5-dioxaspiro[5.5]undecane-9-carboxylate (Ex. XVI-2)

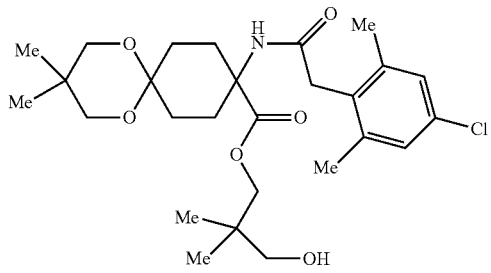 [SMILES: Cc1cc(Cl)cc(C)c1CC(=O)NC1(C(=O)OCC(C)(C)CO)CCC2(CC1)OCC(C)(C)CO2]

12.5 g [120 mmol] of 1,3-dihydroxy-2,2-dimethylpropane and 15 drops of conc. sulfuric acid are added to a solution of 5.067 g [15 mmol] of 1-{[(4-chloro-2,6-dimethylphenyl)acetyl]amino}-4-oxocyclohexanecarboxylic acid in 22.5 ml of chlorobenzene. The reaction mixture is heated at 96 to 105° C. for 4 hours and then, at room temperature, stirred with 25 ml of water and 100 ml of methylene chloride. The organic phase is separated off, washed three times with in each case 25 ml of water, dried over sodium sulfate and concentrated under reduced pressure. This gives 6.51 g of a colourless solid which, according to HPLC, contains 83.5% of the title compound (82.8% of theory).

LC/MS (ESI positive): m/e=510 (MH⁺, 1 ³⁵Cl).
¹H-NMR (600 MHz, CDCl₃): δ=0.92 (s; 6H), 0.94 (s; 6H), 1.3-1.4 (m; 2H), 1.8-1.85 (m; 2H), 1.95-2.1 (m; 4H), 2.30 (s; 6H), 3.32 (s; 2H), 3.45 (d; 4H), 3.56 (s; 2H), 3.97 (s; 2H), 5.42 (s; 1H), 7.1 (s; 2H) ppm.

Example 4

2-Hydroxyethyl 8-[(mesitylacetyl)amino]-1,4-dioxaspiro[4.5]decane-8-carboxylate (Ex. XVI-3)

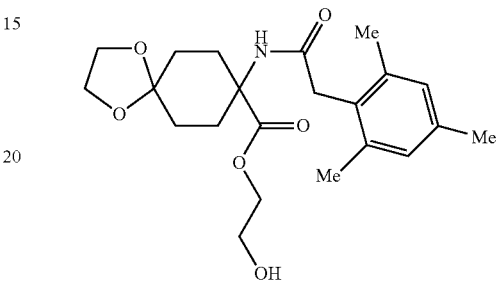

At 85° C., 3 drops of conc. sulfuric acid are added to a suspension of 2.530 g [7 mmol] of 8-[(mesitylacetyl)amino]-1,4-dioxaspiro[4.5]decane-8-carboxylic acid in 19.48 g [313.8 mmol] of ethylene glycol. The reaction mixture is stirred at 100° C. for 3.5 hours and then, at room temperature, taken up in 50 ml of methylene chloride. The methylene chloride phase is separated off and extracted successively with saturated aqueous sodium bicarbonate solution and water, dried over sodium sulfate and concentrated under reduced pressure. This gives 2.90 g of a colourless solid which, according to HPLC, contains 91.9% of the title compound. This corresponds to a yield of 93.9% of theory.

LC/MS (ESI positive): m/e=406 (MH⁺), 811 ([2M+H]⁺).
¹H-NMR (600 MHz, CDCl₃): δ=1.3-1.4 (m; 2H), 1.6-1.7 (m; 2H), 1.85-1.9 (m; 2H), 2.1-2.2 (m; 2H), 2.29 (s; 9H), 3.1 (s, br; 1H), 3.58 (s; 2H), 3.79 (m, br; 2H), 3.91 (s; 4H), 4.3 (m; 2H), 5.61 (s; 1H), 6.92 (s; 2H) ppm.

Example 5

3-Hydroxypropyl 9-{[(4-chloro-2,6-dimethylphenyl)acetyl]amino}-1,5-dioxaspiro[5.5]undecane-9-carboxylate (Ex. XVI-4) and propane-1,3-diyl bis(9-{[(4-chloro-2,6-dimethylphenyl)acetyl]amino}-1,5-dioxaspiro[5.5]undecane-9-carboxylate) (Ex. XVII-4)

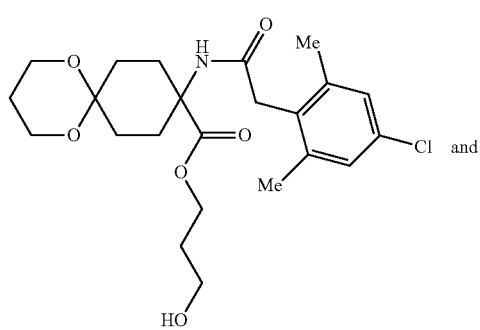

and

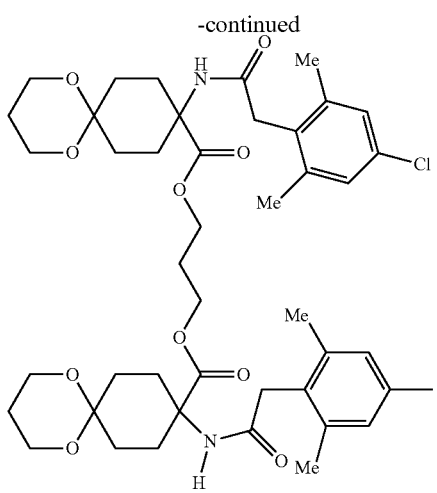

9.31 g [120 mmol] of 1,3-propanediol and 15 drops of conc. sulfuric acid are added to a solution of 5.067 g [15 mmol] of 1-{[(4-chloro-2,6-dimethylphenyl)acetyl]amino}-4-oxocyclohexanecarboxylic acid in 22.5 ml of chlorobenzene. The reaction mixture is heated at 95-100° C. for 10 hours and then, at room temperature, stirred with methylene chloride and water. The organic phase is separated off, washed three times with water, dried over sodium sulfate and concentrated under reduced pressure. This gives 7.37 g of a resinous oil which according to LC/MS, contains 64% of 3-hydroxypropyl 9-{[(4-chloro-2,5-dimethylphenyl)acetyl]amino}-1,5-dioxaspiro[5.5]undecane-9-carboxylate (69% of theory) and 5.2% of propane-1,3-diyl bis(9-{[(4-chloro-2,5-dimethylphenyl)acetyl]amino}-1,5-dioxaspiro[5.5]undecane-9-carboxylate) (6% of theory).

LC/MS (ESI positive): m/e=454 (MH$^+$, 1 $^{35}$Cl), 907 ([2M+H]$^+$, 2 $^{35}$Cl).

LC/MS (ESI positive): m/e=831 (MH$^+$, 2 $^{35}$Cl).

Example 6

11-(4-Chloro-2,6-dimethylphenyl)-12-hydroxy-1,4-dioxa-9-azadispiro[4.2.4.2]tetradec-11-en-10-one (Ex. XI-1)

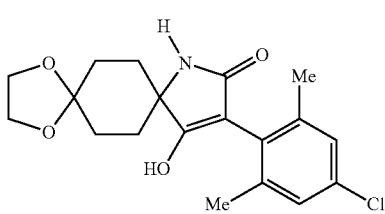 [SMILES: Cc1cc(Cl)cc(C)c1C1=C(O)C2(CCC3(CC2)OCCO3)NC1=O]

A mixture of 1.065 g [2.50 mmol] of 2-hydroxyethyl 8-{[(4-chloro-2,6-dimethylphenyl)acetyl]amino}-1,4-dioxaspiro[4.5]decane-8-carboxylate and 0.218 g [0.28 mmol] of ethane-1,2-diyl bis(8-{[(2,5-dimethylphenyl)acetyl]amino}-1,4-dioxaspiro[4.5]decane-8-carboxylate), prepared as described in Example 1, is initially charged in 5 ml of N,N-dimethylacetamide. At 75-80° C., 1.576 g [8.75 mmol] of a 30% strength solution of sodium methoxide in methanol are then added dropwise over 2 minutes. The reaction mixture is stirred at 75-80° C. for 55 minutes and then concentrated under reduced pressure. The residue is dissolved in 30 ml of water, the solution is filtered and the filtrate is adjusted to pH 4-5 with acetic acid. The precipitated solid is filtered off with suction, washed twice with in each case 5 ml of water and dried. This gives 1.203 g of a light-beige solid which, according to quant. NMR, consists to 80.7% of the title compound. This corresponds to a yield of 99% of theory, based on the sum of both starting material molecules.

$^1$H-NMR (600 MHz, d$_6$-DMSO): δ=1.35-1.4 (m; 2H), 1.65-1.7 (m; 2H), 1.8-1.9 (m; 4H), 2.05-2.15 (m; 2H). 2.07 (s; 6H), 3.88 (s; 4H), 7.09 (s; 2H), 8.1 (s, br; 1H), 10.5 (s, br; 1H) ppm.

Example 7

3-(4-Chloro-2,6-dimethylphenyl)-4-hydroxy-11,11-dimethyl-9,13-dioxa-1-azadispiro[4.2.5.2]pentadec-3-en-2-one (Ex. XI-2)

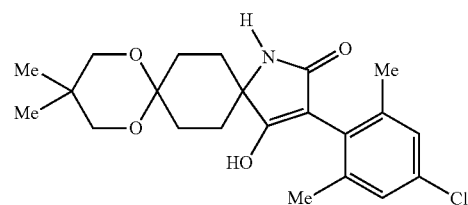 [SMILES: Cc1cc(Cl)cc(C)c1C1=C(O)C2(CCC3(CC2)OCC(C)(C)CO3)NC1=O]

2.550 g [5 mmol] of 3-hydroxy-2,2-dimethylpropyl 9-{[(4-chloro-2,6-dimethylphenyl)acetyl]amino}-3,3-dimethyl-1,5-dioxaspiro[5.5]undecane-9-carboxylate (Example 3) are initially charged in 10 ml of N,N-dimethylacetamide. At 75-80° C., 3.151 g [17.5 mmol] of a 30% strength solution of sodium methoxide in methanol are then added dropwise over 2 minutes. The reaction mixture is stirred at 75-80° C. for 42 minutes and then concentrated under reduced pressure. The residue is dissolved in 60 ml of water and the solution is adjusted to pH 4-5 with acetic acid. The precipitated solid is filtered off with suction, washed twice with in each case 10 ml of water and dried. This gives 2.32 g of a light-beige solid which, according to HPLC, consists to 76% of the title compound. This corresponds to a yield of 86.9% of theory.

LC/MS (ESI positive): m/e=406 (MH$^+$, 1 $^{35}$Cl), 811 ([2M+H]$^+$, 2 $^{35}$Cl).

Example 8

12-Hydroxy-11-mesityl-1,4-dioxa-9-azadispiro[4.2.4.2]tetradec-11-en-10-one (Ex. XI-3)

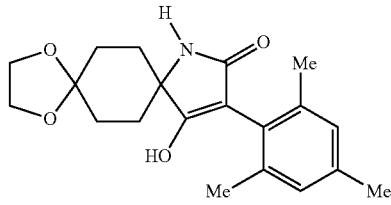 [SMILES: Cc1cc(C)c(C2=C(O)C3(CCC4(CC3)OCCO4)NC2=O)c(C)c1]

2.43 g [6.0 mmol] of 2-hydroxyethyl 8-[(mesitylacetyl)amino]-1,4-dioxaspiro[4.5]decane-8-carboxylate (Example 4) are initially charged in 12 ml of N,N-dimethylacetamide.

At 75-80° C., 3.78 g [21 mmol] of a 30% strength solution of sodium methoxide in methanol are then added dropwise over 3 minutes. The reaction mixture is stirred at 75-80° C. for 6 hours and then concentrated under reduced pressure. The residue is dissolved in 70 ml of water and the solution is adjusted to pH 4 with acetic acid. The precipitated solid is filtered off with suction, washed with 12 ml of water and dried. This gives 1.88 g of a light-beige solid which, according to HPLC, consists to 87% of the title compound. This corresponds to a yield of 79.4% of theory.

LC/MS (ESI positive): m/e=344 (MH$^+$), 687 ([2M+H]$^+$).

$^1$H-NMR (600 MHz, d$_6$-DMSO): δ=1.36-1.38 (m; 2H), 1.67-1.69 (m; 2H), 1.83-1.88 (m; 2H), 2.04 (s; 6H), 2.06-2.1 (m; 2H), 2.2 (s; 3H), 3.88 (s; 4H), 6.81 (s; 2H) ppm.

Example 9

3-Hydroxybutan-2-yl 8-{[(2,5-dimethylphenyl)acetyl]amino}-2,3-dimethyl-1,4-dioxaspiro[4.5]decane-8-carboxylate (Ex. XVI-5)

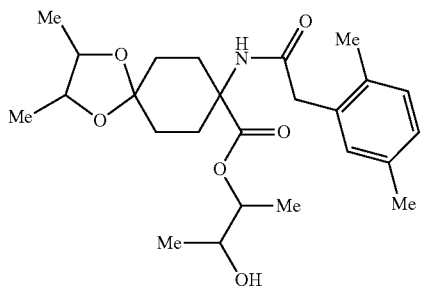 [SMILES: Cc1ccc(C)c(CC(=O)NC2(C(=O)OC(C)C(C)O)CCC3(CC2)OC(C)C(C)O3)c1]

2.87 g [7.66 mmol] of 8-{[(2,5-dimethylphenyl)acetyl]amino}-2,3-dimethyl-1,4-dioxaspiro[4.5]decane-8-carboxylic acid are initially charged in 20 ml of 2,3-butanediol, three drops of conc. sulfuric acid are added and the mixture is stirred at 100° C. for 10 hours. The reaction mixture is then, at room temperature, diluted with methylene chloride and twice extracted with water. The organic phase is dried over sodium sulfate and concentrated under reduced pressure. This gives 4.0 g of a yellowish oil which, according to HPLC, contains 77.1% of the target product, which corresponds to a yield of 90% of theory.

LC/MS (ESI positive): m/e=448 (MH$^+$), 895 ([2M+H]$^+$).

Example 10

11-(2,5-Dimethylphenyl)-12-hydroxy-2,3-dimethyl-1,4-dioxa-9-azadispiro[4.2.4.2]tetradec-11-en-10-one (Ex. XI-4)

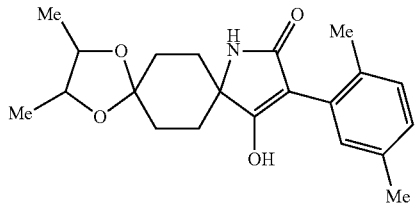 [SMILES: Cc1ccc(C)c(C2=C(O)C3(CCC4(CC3)OC(C)C(C)O4)NC2=O)c1]

1.54 g [3.45 mmol] of 3-hydroxybutan-2-yl 8-{[(2,5-dimethylphenyl)acetyl]amino}-2,3-dimethyl-1,4-dioxaspiro[4.5]decane-8-carboxylate (Example 9) are initially charged in 7 ml of N,N-dimethylacetamide. At 75-80° C., 2.17 g [12.1 mmol] of a 30% strength solution of sodium methoxide in methanol are then added dropwise over 5 minutes. The reaction mixture is stirred at 75-80° C. for 90 minutes and then concentrated under reduced pressure. The residue is dissolved in 40 ml of water and the solution is adjusted to pH 4-5 with acetic acid. The precipitated solid is filtered off with suction, washed twice with in each case 5 ml of water and dried. This gives 0.70 g of a light-beige solid which, according to HPLC, consists to 82.8% of the title compound. This corresponds to a yield of 47.1% of theory.

LC/MS (ESI positive): m/e=358 (MH$^+$), 715 ([2M+H]$^+$).

Example 11

Potassium 8-amino-1,4-dioxaspiro[4.5]decane-8-carboxylate (Ex. XIX-1)

141.4 g [0.625 mol] of 9,12-dioxa-1,3-diazadispiro[4.2.4.2]tetradecane-2,4-dione are suspended in 100 ml of water. Under an atmosphere of argon, the mixture is heated to 90° C., and 298.4 g [2.5 mol] of potassium hydroxide in the form of 47% strength potassium hydroxide solution are added over 15 minutes. The reaction mixture is then stirred under reflux for 24 hours. With further stirring, the mixture is cooled to room temperature and the solid is isolated by filtration through a frit. Drying at 60° C. under a reduced pressure of 1 mbar gives 139.0 g of a beige solid. Quant. NMR: 88.0%. A yield of 81.8% of theory is calculated therefrom.

Example 12

Sodium 8-amino-1,4-dioxaspiro[4.5]decane-8-carboxylate (Ex. XIX-2)

43.4 g [0.192 mol] of 9,12-dioxa-1,3-diazadispiro[4.2.4.2]tetradecane-2,4-dione are suspended in 30 ml of water. Under an atmosphere of argon, the mixture is heated to 90° C., and 68.3 g [0.768 mol] of sodium hydroxide in the form of 45% strength sodium hydroxide solution are added over 2 minutes. The reaction mixture is then stirred under reflux for 27.5 hours. With further stirring, the mixture is cooled to room temperature and the solid is isolated by filtration through a frit. Drying at 60° C. under a reduced pressure of 1 mbar gives 54.8 g of a beige solid. Quant. NMR: 72.7%. A yield of 93.0% of theory is calculated therefrom.

$^1$H-NMR (600 MHz, D$_2$O): δ=1.56-1.6 (m, 2H), 1.69-1.75 (m, 2H), 1.75-1.82 (m, 2H), 2.0-2.04 (m, 2H), 4.06 (s, 4H) ppm.

Example 13

Sodium 8-amino-1,4-dioxaspiro[4.5]decane-8-carboxylate (Ex. XIX-2)

291.8 g [1.29] of 9,12-dioxa-1,3-diazadispiro[4.2.4.2]tetradecane-2,4-dione are suspended in 495 ml of water. Under an atmosphere of argon, the mixture is heated to 90° C., and 773.3 g [8.7 mol] of sodium hydroxide in the form of 45% strength sodium hydroxide solution are added over 17 minutes. The reaction mixture is then stirred under reflux for 20 hours. With further stirring, the mixture is cooled to room temperature and the solid is isolated by filtration through a frit. Drying at 60° C. under a reduced pressure of 1 mbar gives 367.3 g of a beige solid. Quant. NMR: 76.3%. A yield of 97.1% of theory is calculated therefrom.

Example 14

1-{[(4-Chloro-2,6-dimethylphenyl)acetyl]amino}-4-oxocyclohexanecarboxylic acid (Ex. XV-1)

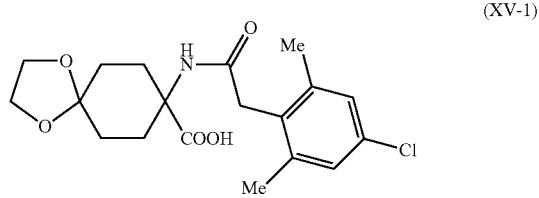 [SMILES: Cc1cc(Cl)cc(C)c1CC(=O)NC1(C(=O)O)CCC2(CC1)OCCO2]
(XV-1)

At room temperature, 23.88 g [81.4 mmol] of potassium 8-amino-1,4-dioxaspiro[4.5]decane-8-carboxylate of a purity of 81.6% according to quant. NMR are initially charged in 65 ml of water, resulting in a pH of about 13.6. The solution is cooled to 2° C. and adjusted to pH 12.1 with 32% strength hydrochloric acid. At 3 to 5° C., a solution of 17.68 g [81.4 mmol] of (4-chloro-2,6-dimethylphenyl)acetyl chloride in 20 ml of dry tetrahydrofuran is then added dropwise over 70 minutes. At the same time, 32% strength aqueous sodium hydroxide solution is added dropwise at such a rate that the pH of the reaction mixture remains between 11.8 and 12.5 at all times (consumption 10.93 g [87.4 mmol]). Stirring is then continued at 3 to 5° C. for 60 minutes, the mixture is allowed to warm to room temperature and diluted with 30 ml of water and the pH of the reaction mixture is adjusted to about 1.8 with effective stirring. The precipitated solid is washed twice with in each case 30 ml of water and then dried at about 60° C. under reduced pressure. This gives 29.31 g of an almost colourless solid.

Quant. NMR: 88.7% pure, which corresponds to a yield of 83.6% of theory.

$^1$H-NMR (600 MHz, d$_6$-DMSO): δ=1.56-1.58 (m, 2H), 1.64-1.69 (m, 2H), 1.84-1.9 (m, 2H), 2.01-2.03 (m, 2H), 2.24 (s, 6H), 3.54 (s, 2H), 3.86 (s, 4H), 7.05 (s, 2H), 8.17 (s, 1H), 12 (s, br, 1H) ppm.

Comparative Example 1

Methyl 8-amino-1,4-dioxaspiro[4.5]decane-8-carboxylate

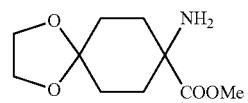

At 5 to 10° C., 57 g of thionyl chloride are added dropwise to a suspension of 64.5 g of 8-amino-1,4-dioxaspiro[4.5]decane-8-carboxylic acid in 960 ml of methanol over 60 minutes. The mixture is warmed to 40 to 45° C. and stirred at this temperature for 48 hours. After cooling to 5° C., the solid is filtered off with suction, washed with 60 ml of cold methanol and dried. With stirring, the solid is then introduced into a solution of 54 g of potassium carbonate in 220 ml of water and stirred for about 30 minutes. The mixture is then extracted five times with in each case 200 ml of methylene chloride. The combined organic phases are dried over sodium sulfate and concentrated on a rotary evaporator at 30° C. This gives 65.8 g of a dark oil which, according to GC/MS after silylation, contains approximately 52.7% of the title

Comparative Example 2

Methyl 8-{[(4-chloro-2,6-dimethylphenyl)acetyl]amino}-1,4-dioxaspiro[4.5]decane-8-carboxylate

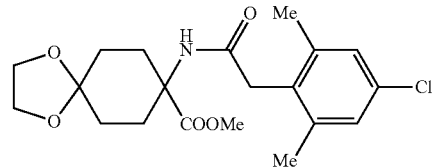 [SMILES: COC(=O)C1(NC(=O)Cc2c(C)cc(Cl)cc2C)CCC2(CC1)OCCO2]

At room temperature, 38 g of potassium carbonate are added to a solution of 33.4 g of the product from Comparative example 1 in 490 ml of dry acetonitrile. At a temperature of 5 to 10° C., a solution of 30 g of (4-chloro-2,6-dimethylphenyl)acetyl chloride in 60 ml of dry acetonitrile is then metered in over 1 hour. Stirring is continued at 5° C. for 2 hours and at room temperature overnight, the reaction mixture is added to about 2 litres of water and stirred at room temperature for 1 hour and the precipitated solid is filtered off, washed with 250 ml of water and dried at 50° C. under reduced pressure. This gives 53.2 g of a white solid which, according to GC, contains 66.4% of the title compound, 18.2% of methyl 1-{[(4-chloro-2,6-dimethylphenyl)acetyl]amino}-4,4-dimethoxycyclohexanecarboxylate and 12.4% of methyl 1-{[(4-chloro-2,6-dimethylphenyl)acetyl]amino}-4-oxocyclohexanecarboxylate.

Comparative Example 3

Methyl 8-{[(4-chloro-2,6-dimethylphenyl)acetyl]amino}-1,4-dioxaspiro[4.5]decane-8-carboxylate

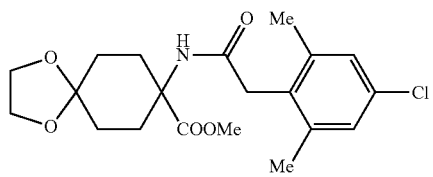 [SMILES: COC(=O)C1(NC(=O)Cc2c(C)cc(Cl)cc2C)CCC2(CC1)OCCO2]

A solution of 28.0 g of crude methyl 8-amino-1,4-dioxaspiro[4.5]decane-8-carboxylate hydrochloride, which is about 69% pure and additionally comprises about 21% of methyl 1-amino-4,4-dimethoxycyclohexanecarboxylate, in 90 ml of water is cooled to 10° C. and adjusted to a pH of about 7.2 using 1 N aqueous sodium hydroxide solution. 10.92 g of sodium bicarbonate and 100 ml of xylene are added, followed by the dropwise addition, over 1 hour and at 5 to 10° C., of a solution of 23.88 g of (4-chloro-2,6-dimethylphenyl)acetyl chloride in 27 ml of xylene. Stirring is subsequently continued at 5 to 10° C. for 30 minutes, and the mixture is then warmed to 65° C. and stirred at this temperature for 1 hour. During this time, the pH is kept at 7 by addition of 1 N aqueous sodium hydroxide solution. After cooling to room temperature, the precipitated solid is filtered off with suction and washed successively with 25 ml of xylene and twice with in each case 25 ml of petroleum ether. Drying under reduced pressure at 50° C. gives a beige solid which, according to HPLC analysis, contains 78.8% of the title compound, 6.6% of methyl 1-{[(4-chloro-2,6-dimethylphenyl)acetyl]amino}-4,4-dimethoxycyclohexanecarboxylate and 11.1% of methyl 1-{[(4-chloro-2,6-dimethylphenyl)acetyl]amino}-4-oxocyclohexanecarboxylate.

Comparative Example 4

11-(4-Chloro-2,6-dimethylphenyl)-12-hydroxy-1,4-dioxa-9-azadispiro[4.2.4.2]tetradec-11-en-10-one

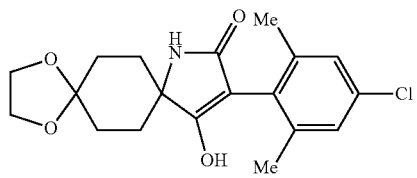 [SMILES: Cc1cc(Cl)cc(C)c1C1=C(O)C2(CCC3(CC2)OCCO3)NC1=O]

A solution of 42.0 g of crude methyl 8-amino-1,4-dioxaspiro[4.5]decane-8-carboxylate hydrochloride, which is about 69% pure and additionally comprises about 21% of methyl 1-amino-4,4-dimethoxycyclohexanecarboxylate, in 135 ml of water is cooled to 10° C. and adjusted to a pH of about 7.2 using 1 N aqueous sodium hydroxide solution. 16.4 g of sodium bicarbonate and 150 ml of xylene are added, followed by the dropwise addition, over 1 hour and at 5 to 10° C., of a solution of 29.31 g of (4-chloro-2,6-dimethylphenyl)acetyl chloride in 36 ml of xylene. Stirring is subsequently continued at 5 to 10° C. for 30 minutes, and the mixture is then warmed to 65° C. and stirred at this temperature for 1 hour. During this time, the pH is kept at 7 by addition of 1 N aqueous sodium hydroxide solution. Subsequently, the water is removed by azeotropic distillation on a water separator under reduced pressure of about 250 to 110 mbar. The bottom is allowed to cool to about 50° C., and 110 ml of N,N-dimethylacetamide are then added. The xylene is then distilled off under slightly reduced pressure at a boiling point of about 70° C. The mixture is then cooled to 50° C., and 36.47 g of 30% strength methanolic sodium methoxide solution are then added dropwise over 10 minutes. The mixture is heated to 70° C. and the methanol is distilled off under slightly reduced pressure over about 2 hours. Under reduced pressure, the N,N-dimethylacetamide is then substantially distilled off. The residue is taken up in 500 ml of water and the solution is adjusted to a pH of about 5 by addition of glacial acetic acid. The precipitated solid is filtered off with suction, washed twice with in each case 80 ml of water and dried at 50° C. under reduced pressure. This gives 51.95 g of a beige solid which, according to LC/MS analysis, contains 71.3% of the title compound, 11.1% of 3-(4-chloro-2,6-dimethylphenyl)-4-hydroxy-8,8-dimethoxy-1-azaspiro[4.5]dec-3-en-2-one and 1.9% of 3-(4-chloro-2,6-dimethylphenyl)-4-hydroxy-1-azaspiro[4.5]dec-3-ene-2,8-dione.

The invention claimed is:
1. Process for preparing one or more compounds of formula (XI)

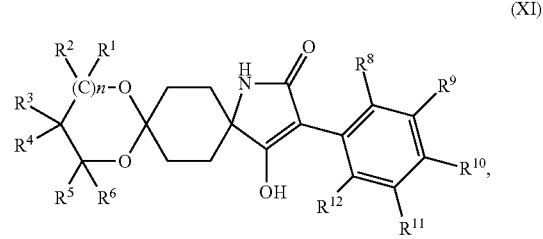

where
$R^1$, $R^2$, $R^3$, $R^4$, $R^5$, $R^6$ independently of one another represent hydrogen, methyl, ethyl or phenyl,
$R^8$, $R^9$, $R^{10}$, $R^{11}$, $R^{12}$ independently of one another represent hydrogen, methyl, ethyl, fluoroalkyl having one or 2 carbon atoms and one to five fluorine atoms, halogen, methoxy, ethoxy, trifluoromethoxy or optionally methyl-, ethyl-, methoxy-, ethoxy- or halogen-substituted phenyl
and
n represents 0 or 1,
comprising reacting one or more compounds of formula (III)

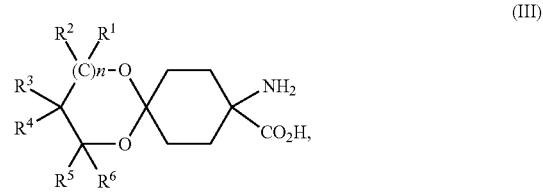

where n and $R^1$ to $R^6$ have the meanings given above,
in the presence of a base with one or more compounds of the formula (VII)

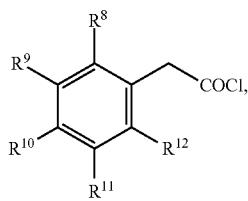

where $R^8$ to $R^{12}$ have the meanings given above, to give one or more compounds of formula (XV)

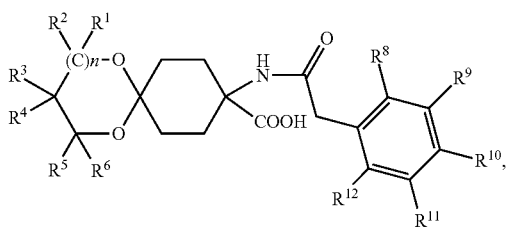

(XV)

where n, $R^1$ to $R^6$ and $R^8$ to $R^{12}$ have the meanings given above;

one or more compounds of formula (XV) are then esterified with one or more compounds of formula (XIV)

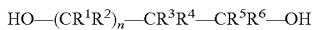

$$HO-(CR^1R^2)_n-CR^3R^4-CR^5R^6-OH \quad (XIV),$$

where n and $R^1$ to $R^6$ have the meanings given above and are identical to those in the compound of the general formula (XV), in the presence of an acid as catalyst, to give one or more compounds of formulae (XVI) and (XVII)

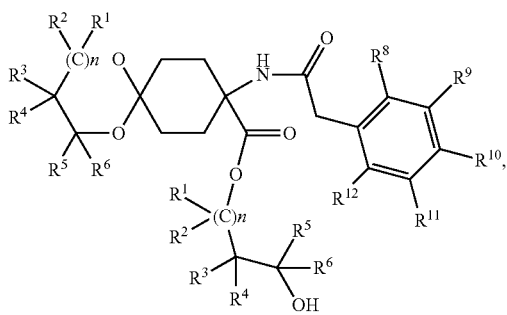

(XVI)

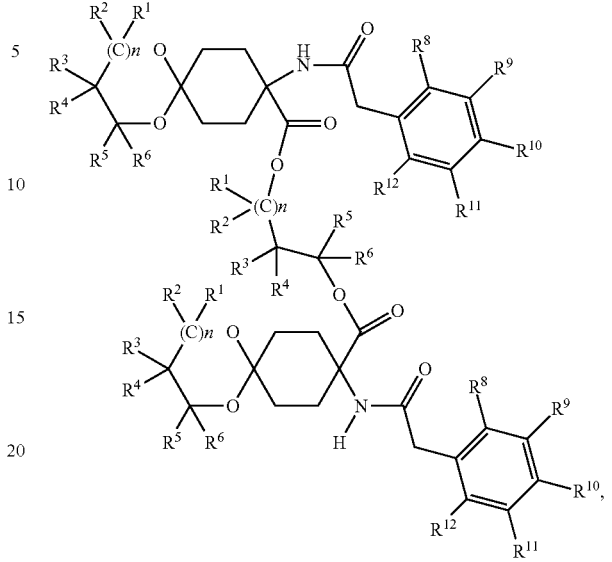

(XVII)

where n, $R^1$ to $R^6$ and $R^8$ to $R^{12}$ have the meanings given above and both n and the radicals $R^1$ to $R^6$ and $R^8$ to $R^{12}$ of the compound of formula (XVI) are identical to the corresponding radicals $R^1$ to $R^6$ and $R^8$ to $R^{12}$ of the compound of the formula (XVII);

converting one or more compounds of the formulae (XVI) and (XVII) in which n, $R^1$ to $R^6$ and $R^8$ to $R^{12}$ have the meanings given above, by reaction with a strong base into one or more compounds of formula (XI)

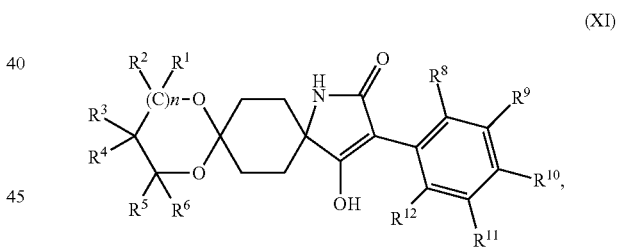

(XI)

where n, $R^1$ to $R^6$ and $R^8$ to $R^{12}$ have the meanings given above.

2. Process according to claim 1, where
$R^1$ to $R^6$ independently of one another represent hydrogen, methyl or ethyl,
$R^8$ to $R^{12}$ independently of one another represent hydrogen, methyl, ethyl, fluorine, chlorine, methoxy, ethoxy, trifluoromethoxy or optionally methyl-, ethyl-, methoxy-, ethoxy-, fluorine-, chlorine- or bromine-substituted phenyl
n represents 0 or 1.

3. Process according to claim 1, where
$R^1$ to $R^6$ independently of one another represent hydrogen or methyl,
$R^8$ to $R^{12}$ independently of one another represent hydrogen, methyl, ethyl, fluorine, chlorine, methoxy, ethoxy or optionally methyl-, ethyl-, methoxy-, ethoxy-, fluorine- or chlorine-substituted phenyl,
n represents 0 or 1.

4. Process for preparing one or more compounds of formula (XIX)

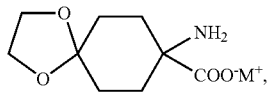
(XIX)

where

M represents sodium or potassium, comprising reacting 9,12-dioxa-1,3-diazadispiro[4.2.4.2]tetradecane-2,4-dione with aqueous sodium hydroxide solution or aqueous potassium hydroxide solution, where the sodium hydroxide or potassium hydroxide is employed in an amount from 1 to 10 molar equivalents and a product of the formula (XIX) is isolated by filtration.

5. Process for preparing one or more compounds of the formulae (XVI) and (XVII)

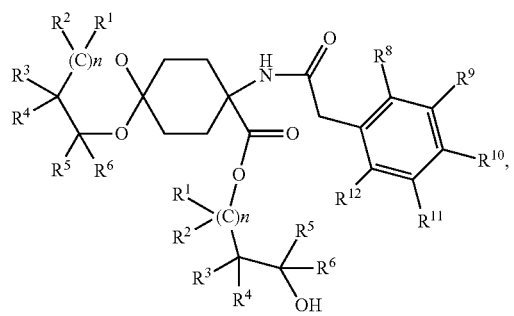
(XVI)

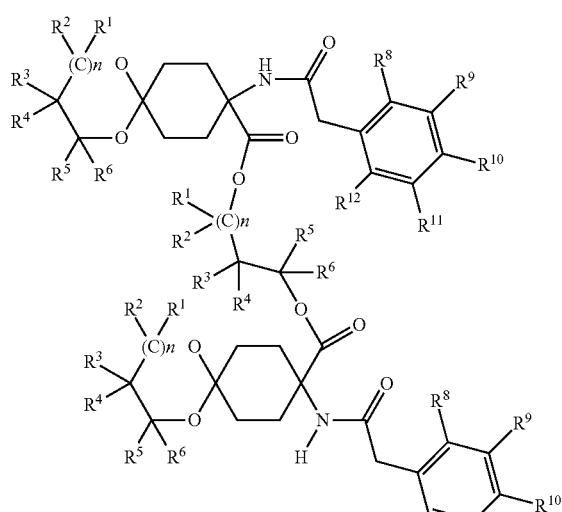
(XVII)

where $R^1$, $R^2$, $R^3$, $R^4$, $R^5$, $R^6$ independently of one another represent hydrogen, methyl, ethyl or phenyl, $R^8$, $R^9$, $R^{10}$, $R^{11}$, $R^{12}$ independently of one another represent hydrogen, methyl, ethyl, fluoroalkyl having one or 2 carbon atoms and one to 5 fluorine atoms, halogen, methoxy, ethoxy, trifluoromethoxy or optionally methyl-, ethyl-, methoxy-, ethoxy- or halogen-substituted phenyl, the radicals $R^1$ to $R^6$ and $R^8$ to $R^{12}$ of the compound of formula (XVI) are identical to the corresponding radicals $R^1$ to $R^6$ and $R^8$ to $R^{12}$ of the compound of formula (XVII) and n represents 0 or 1 and is identical for the compounds of the formulae (XVI) and (XVII)

comprising reacting a compound of formula (XVIII)

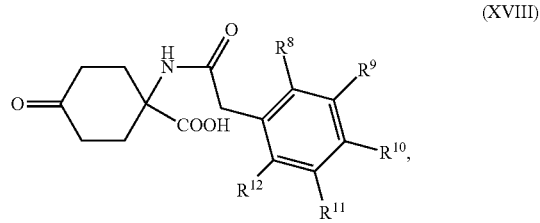
(XVIII)

where $R^8$ to $R^{12}$ have the meanings given above, with one or more compounds of formula (XIV)

$$HO—(CR^1R^2)_n—CR^3R^4—CR^5R^6—OH \quad (XIV),$$

where n and $R^1$ to $R^6$ have the meanings given above and n and the radicals $R^1$ to $R^6$ of the compound of formula (XIV) are identical to n and the corresponding radicals $R^1$ to $R^6$ of the compounds of the formulae (XVI) and (XVII), in the presence of an acid as catalyst.

6. Compound of formula (XV-1)

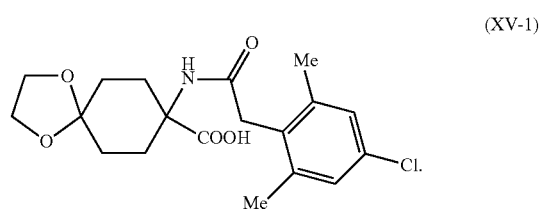 [SMILES: Cc1cc(Cl)cc(C)c1CC(=O)NC1(C(=O)O)CCC2(CC1)OCCO2]
(XV-1)

7. Compounds of formulae (XVI) and (XVII)

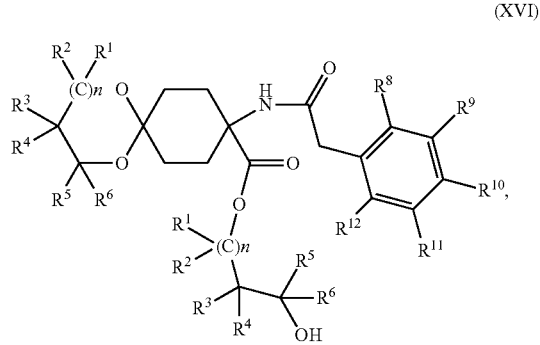
(XVI)

-continued (XVII)

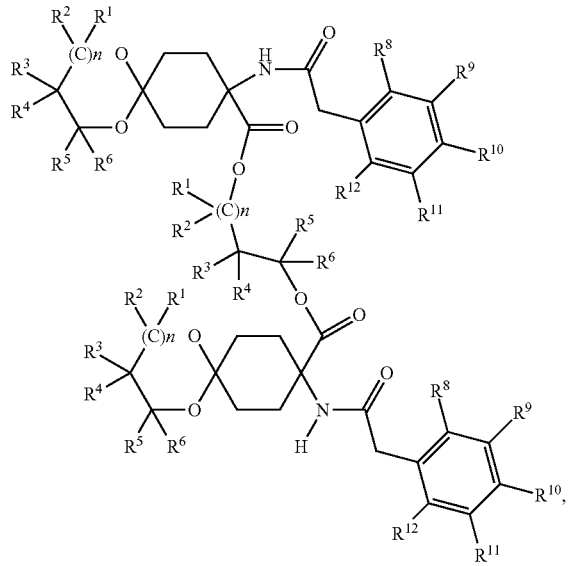

where
$R^1$ to $R^6$ independently of one another represent hydrogen, methyl, ethyl or phenyl and the radicals $R^1$ to $R^6$ of the compound of the formula (XVI) are identical to the corresponding radicals $R^1$ to $R^6$ of the compound of formulae (XVII), n represents 0 or 1 and is identical in the compounds of formulae (XVI) and (XVII),
and
$R^8$ to $R^{12}$ independently of one another represent hydrogen, methyl, ethyl, fluoroalkyl having one or 2 carbon atoms and one to five fluorine atoms, halogen, methoxy, ethoxy, trifluoromethoxy or optionally methyl-, ethyl-, methoxy-, ethoxy- or halogen-substituted phenyl
and the radicals $R^8$ to $R^{12}$ of the compound of the formula (XVI) are identical to the corresponding radicals $R^8$ to $R^{12}$ of the compound of the formulae (XVII).

8. Compounds of formulae (XVI) and (XVII) according to claim 7
where
$R^3$ to $R^6$ independently of one another represent hydrogen or methyl,
n represents 0
and
$R^8$ to $R^{12}$ independently of one another represent hydrogen, methyl or chlorine.

9. Compounds of formulae (XVI) and (XVII) according to claim 7
in which
$R^3$ to $R^6$ represent hydrogen,
n represents 0 and
$R^8$ represents methyl,
$R^9$ represents hydrogen,
$R^{10}$ represents chlorine,
$R^{11}$ represents hydrogen,
$R^{12}$ represents methyl.

\* \* \* \* \*